US009050365B2

(12) United States Patent
Fossel

(10) Patent No.: US 9,050,365 B2
(45) Date of Patent: *Jun. 9, 2015

(54) TRANSDERMAL DELIVERY OF BENEFICIAL SUBSTANCES EFFECTED BY A HOSTILE BIOPHYSICAL ENVIRONMENT

(75) Inventor: Eric Thor Fossel, Cambridge, MA (US)

(73) Assignee: Strategic Science & Technologies, LLC, Cambridge, MA (US)

( * ) Notice: Subject to any disclaimer, the term of this patent is extended or adjusted under 35 U.S.C. 154(b) by 330 days.

This patent is subject to a terminal disclaimer.

(21) Appl. No.: 11/587,323

(22) PCT Filed: Apr. 19, 2005

(86) PCT No.: PCT/US2005/013228
§ 371 (c)(1),
(2), (4) Date: Aug. 21, 2007

(87) PCT Pub. No.: WO2005/102282
PCT Pub. Date: Nov. 3, 2005

(65) Prior Publication Data
US 2008/0280984 A1    Nov. 13, 2008

Related U.S. Application Data

(60) Provisional application No. 60/563,573, filed on Apr. 19, 2004, provisional application No. 60/563,575, filed on Apr. 19, 2004, provisional application No. 60/563,574, filed on Apr. 19, 2004, provisional application No. 60/563,558, filed on Apr. 19, 2004, provisional application No. 60/563,559, filed on Apr. 19, 2004, provisional application No. 60/563,560, filed on Apr. 19, 2004, provisional application No. 60/563,576, filed on Apr. 19, 2004, provisional application No. 60/563,572, filed on Apr. 19, 2004, provisional application No. 60/563,564, filed on Apr. 19, 2004, provisional application No. 60/563,570, filed on Apr. 19, 2004, provisional application No. 60/563,561, filed on Apr. 19, 2004, provisional application No. 60/563,562, filed on Apr. 19, 2004, provisional application No. 60/563,567, filed on Apr. 19, 2004, provisional application No. 60/563,552, filed on Apr. 19, 2004, provisional application No. 60/563,569, filed on Apr. 19, 2004, provisional application No. 60/563,571, filed on Apr. 19, 2004, provisional application No. 60/563,563, filed on Apr. 19, 2004, provisional application No. 60/563,565, filed on Apr. 19, 2004, provisional application No. 60/563,566, filed on Apr. 19, 2004, provisional application No. 60/563,553, filed on Apr. 19, 2004, provisional application No. 60/563,554, filed on Apr. 19, 2004, provisional application No. 60/563,555, filed on Apr. 19, 2004, provisional application No. 60/563,556, filed on Apr. 19, 2004, provisional application No. 60/563,557, filed on Apr. 19, 2004, provisional application No. 60/563,551, filed on Apr. 19, 2004.

(51) Int. Cl.
*A61K 31/195* (2006.01)
*A61K 47/18* (2006.01)
*A61K 9/00* (2006.01)
*A61K 47/02* (2006.01)
*A61K 31/192* (2006.01)
*A61K 31/519* (2006.01)
*A61K 31/198* (2006.01)
*A61K 31/522* (2006.01)
*A61K 9/06* (2006.01)
*A61K 47/06* (2006.01)
*A61K 47/10* (2006.01)
*A61K 47/14* (2006.01)
*A61K 47/26* (2006.01)

(52) U.S. Cl.
CPC ............... *A61K 47/18* (2013.01); *A61K 9/0014* (2013.01); *A61K 47/02* (2013.01); *A61K 47/183* (2013.01); *A61K 31/192* (2013.01); *A61K 31/519* (2013.01); *A61K 31/198* (2013.01); *A61K 31/522* (2013.01); *A61K 9/06* (2013.01); *A61K 47/06* (2013.01); *A61K 47/10* (2013.01); *A61K 47/14* (2013.01); *A61K 47/26* (2013.01)

(58) Field of Classification Search
None
See application file for complete search history.

(56) References Cited

U.S. PATENT DOCUMENTS 3,574,854 A    4/1971   Bossard
3,960,782 A    6/1976   Daley et al.
(Continued)

FOREIGN PATENT DOCUMENTS

CA    2337772       1/2000
CN    101340916 A   1/2009
(Continued)

OTHER PUBLICATIONS

Tiso et al (Pain Physician 13:457-467, 2010).*
(Continued)

*Primary Examiner* — Craig Ricci
(74) *Attorney, Agent, or Firm* — Wolf, Greenfield & Sacks, P.C.

(57) ABSTRACT

The present invention generally relates to the transdermal delivery of substances and, in some embodiments, to the transdermal delivery of beneficial substances by a hostile biophysical environment. In one aspect, various methods for the transdermal delivery of beneficial substances are disclosed. By creating a hostile biophysical environment, beneficial substances may be delivered, according to certain embodiments, through the stratum corneum of the skin into the body. Beneficial substances include, but are not limited to, pharmaceutical agents, drugs, vitamins, co-factors, peptides, dietary supplements, and others. The beneficial effects disclosed include, for instance, relief of pain and inflammation, prevention and healing of ulcers of the skin, relief of headache, improved sexual function and enjoyment, growth of hair on the scalp, improving muscle size and/or function, removing body fat and/or cellulite, treating cancer, treating viral infections and others.

19 Claims, No Drawings

(56) References Cited

U.S. PATENT DOCUMENTS

| | | | |
|---|---|---|---|
| 4,185,100 A | 1/1980 | Rovee et al. | |
| 4,681,897 A | 7/1987 | Brand | |
| 4,692,462 A | 9/1987 | Banerjee | |
| 4,702,913 A | 10/1987 | Marty | |
| 4,722,837 A | 2/1988 | Cameron | |
| 4,732,892 A | 3/1988 | Sarpotdar et al. | |
| 4,743,442 A | 5/1988 | Raaf et al. | |
| 4,871,839 A | 10/1989 | Gibson | |
| 4,940,456 A | 7/1990 | Sibalis et al. | |
| 4,945,901 A | 8/1990 | Burcke, Jr. | |
| 4,950,654 A | 8/1990 | Horn et al. | |
| 4,976,952 A | 12/1990 | Lang et al. | |
| 5,008,248 A | 4/1991 | Bywater et al. | |
| 5,028,435 A | 7/1991 | Katz et al. | |
| 5,158,761 A | 10/1992 | Kamishita et al. | |
| 5,180,743 A | 1/1993 | Watanabe et al. | |
| 5,210,099 A * | 5/1993 | Mody et al. | 514/557 |
| 5,215,759 A | 6/1993 | Mausner | |
| 5,217,652 A | 6/1993 | Iovanni | |
| 5,217,997 A | 6/1993 | Levere et al. | |
| 5,254,331 A | 10/1993 | Mausner | |
| 5,256,678 A | 10/1993 | Nakaguchi | |
| 5,332,758 A | 7/1994 | Nakata et al. | |
| 5,391,550 A | 2/1995 | Carniglia et al. | |
| 5,405,919 A | 4/1995 | Keefer et al. | |
| 5,428,070 A | 6/1995 | Cooke et al. | |
| 5,439,938 A | 8/1995 | Snyder et al. | |
| 5,464,954 A | 11/1995 | Kimura et al. | |
| 5,476,852 A | 12/1995 | Cauwenbergh | |
| 5,498,420 A | 3/1996 | Edgar et al. | |
| 5,505,958 A * | 4/1996 | Bello et al. | 424/449 |
| 5,527,797 A | 6/1996 | Eisenberg et al. | |
| 5,538,740 A | 7/1996 | Abad | |
| 5,543,430 A | 8/1996 | Kaesemeyer | |
| 5,573,776 A | 11/1996 | Harrison et al. | |
| 5,576,351 A | 11/1996 | Yoshimura et al. | |
| 5,595,753 A | 1/1997 | Hechtman | |
| 5,605,685 A | 2/1997 | Tseng et al. | |
| 5,629,002 A | 5/1997 | Weuffen et al. | |
| 5,632,981 A | 5/1997 | Saavedra et al. | |
| 5,643,586 A | 7/1997 | Perricone | |
| 5,645,859 A | 7/1997 | Chaudhuri et al. | |
| 5,648,101 A | 7/1997 | Tawashi | |
| 5,656,264 A | 8/1997 | Hanada et al. | |
| 5,691,423 A | 11/1997 | Smith et al. | |
| 5,698,738 A | 12/1997 | Garfield et al. | |
| 5,714,472 A | 2/1998 | Gray et al. | |
| 5,762,963 A * | 6/1998 | Byas-Smith | 424/472 |
| 5,789,442 A | 8/1998 | Garfield et al. | |
| 5,807,957 A | 9/1998 | Samour et al. | |
| 5,824,658 A | 10/1998 | Falk et al. | |
| 5,853,768 A | 12/1998 | Altadonna | |
| 5,891,459 A | 4/1999 | Cooke et al. | |
| 5,891,472 A * | 4/1999 | Russell | 424/484 |
| 5,895,658 A | 4/1999 | Fossel | |
| 5,906,822 A | 5/1999 | Samour et al. | |
| 5,911,980 A | 6/1999 | Samour et al. | |
| 5,922,332 A * | 7/1999 | Fossel | 424/401 |
| 5,925,372 A | 7/1999 | Berner et al. | |
| 5,939,094 A | 8/1999 | Durif et al. | |
| 5,976,566 A | 11/1999 | Samour et al. | |
| 5,985,317 A | 11/1999 | Venkateshwaran et al. | |
| 6,036,977 A | 3/2000 | Drizen et al. | |
| 6,037,346 A | 3/2000 | Doherty, Jr. et al. | |
| 6,103,275 A | 8/2000 | Seitz et al. | |
| 6,117,872 A | 9/2000 | Maxwell et al. | |
| 6,207,713 B1 | 3/2001 | Fossel | |
| 6,242,229 B1 | 6/2001 | Pineau et al. | |
| 6,264,979 B1 | 7/2001 | Svedman | |
| 6,287,601 B1 | 9/2001 | Russell | |
| 6,312,720 B1 | 11/2001 | Katinger et al. | |
| 6,375,672 B1 | 4/2002 | Aksan et al. | |
| 6,387,081 B1 | 5/2002 | Cooper | |
| 6,444,234 B1 | 9/2002 | Kirby et al. | |
| 6,448,267 B1 | 9/2002 | Anggard et al. | |
| 6,451,337 B1 | 9/2002 | Smith et al. | |
| 6,458,841 B2 | 10/2002 | Fossel | |
| 6,469,012 B1 | 10/2002 | Ellis et al. | |
| 6,511,991 B2 | 1/2003 | Hrabie et al. | |
| 6,538,033 B2 | 3/2003 | Bing | |
| 6,558,695 B2 | 5/2003 | Luo et al. | |
| 6,562,370 B2 | 5/2003 | Luo et al. | |
| 6,565,879 B1 | 5/2003 | Luo et al. | |
| 6,582,724 B2 | 6/2003 | Hsu et al. | |
| 6,586,000 B2 | 7/2003 | Luo et al. | |
| 6,602,912 B2 | 8/2003 | Hsu et al. | |
| 6,617,337 B1 | 9/2003 | Wilcox | |
| 6,642,260 B2 | 11/2003 | Haj-Yehia | |
| 6,646,006 B2 | 11/2003 | Cooke et al. | |
| 6,676,962 B1 | 1/2004 | Muller | |
| 6,716,436 B1 | 4/2004 | Seguin | |
| 6,719,997 B2 | 4/2004 | Hsu et al. | |
| 6,747,063 B2 | 6/2004 | Adams et al. | |
| 6,787,152 B2 | 9/2004 | Kirby et al. | |
| 6,835,392 B2 | 12/2004 | Hsu et al. | |
| 6,858,232 B2 | 2/2005 | Verbiscar | |
| 7,241,456 B2 | 7/2007 | Vromen | |
| 7,267,829 B2 | 9/2007 | Kirby et al. | |
| 7,442,690 B2 | 10/2008 | Prejean et al. | |
| 7,629,384 B2 | 12/2009 | Fossel | |
| 7,914,814 B2 | 3/2011 | Fossel | |
| 8,603,519 B2 | 12/2013 | Fossel | |
| 8,604,081 B2 | 12/2013 | Fossel | |
| 2002/0015713 A1 | 2/2002 | Murdock et al. | |
| 2002/0037854 A1 | 3/2002 | Breton et al. | |
| 2002/0041903 A1 * | 4/2002 | Fossel | 424/718 |
| 2002/0168325 A1 | 11/2002 | Lerner et al. | |
| 2002/0168424 A1 | 11/2002 | Shahinpoor et al. | |
| 2003/0018076 A1 | 1/2003 | Fossel | |
| 2003/0028169 A1 | 2/2003 | Fossel | |
| 2003/0044439 A1 | 3/2003 | Dobson et al. | |
| 2003/0069618 A1 | 4/2003 | Smith et al. | |
| 2003/0157185 A1 | 8/2003 | Paradise | |
| 2003/0203915 A1 | 10/2003 | Fang et al. | |
| 2004/0082659 A1 | 4/2004 | Cooke et al. | |
| 2004/0228908 A1 | 11/2004 | Liu et al. | |
| 2005/0069590 A1 | 3/2005 | Buehler et al. | |
| 2005/0196418 A1 | 9/2005 | Yu et al. | |
| 2007/0065463 A1 | 3/2007 | Aung-Din et al. | |
| 2007/0072847 A1 | 3/2007 | Mueller et al. | |
| 2007/0087977 A1 | 4/2007 | Robbins | |
| 2007/0105763 A1 | 5/2007 | Ghosh | |
| 2007/0253911 A1 | 11/2007 | Tamarkin et al. | |
| 2008/0045909 A1 | 2/2008 | Fossel | |
| 2008/0233183 A1 | 9/2008 | McCook et al. | |
| 2008/0292684 A1 | 11/2008 | Colombo et al. | |
| 2009/0105336 A1 | 4/2009 | Fossel | |
| 2009/0123528 A1 | 5/2009 | Fossel | |
| 2009/0142390 A1 | 6/2009 | Jackson et al. | |
| 2009/0221536 A1 | 9/2009 | Fossel | |
| 2009/0247635 A1 | 10/2009 | Ehrenpreis | |
| 2010/0196332 A1 | 8/2010 | Wichterle et al. | |
| 2010/0196517 A1 | 8/2010 | Fossel | |
| 2010/0280122 A1 | 11/2010 | Fossel | |
| 2010/0291195 A1 | 11/2010 | Fossel | |
| 2010/0291236 A1 | 11/2010 | Sadler et al. | |
| 2010/0316749 A1 | 12/2010 | Fossel | |
| 2010/0317737 A1 | 12/2010 | Fossel | |
| 2011/0028548 A1 | 2/2011 | Fossel | |
| 2011/0182977 A1 | 7/2011 | Fossel | |
| 2012/0108664 A1 | 5/2012 | Fossel | |
| 2012/0148665 A1 | 6/2012 | Fossel | |
| 2012/0258865 A1 | 10/2012 | Short et al. | |
| 2013/0072498 A1 | 3/2013 | Fossel | |
| 2013/0289059 A1 | 10/2013 | Fossel | |
| 2014/0004176 A1 | 1/2014 | Fossel | |
| 2014/0004177 A1 | 1/2014 | Fossel | |
| 2014/0010866 A1 | 1/2014 | Fossel | |
| 2014/0038205 A1 | 2/2014 | Raynard | |
| 2014/0044774 A1 | 2/2014 | Fossel | |
| 2014/0051707 A1 | 2/2014 | Fossel | |
| 2014/0051717 A1 | 2/2014 | Fossel | |
| 2014/0056971 A1 | 2/2014 | Fossel | |
| 2014/0066452 A1 | 3/2014 | Fossel | |

(56) References Cited

U.S. PATENT DOCUMENTS

| | | |
|---|---|---|
| 2014/0066511 A1 | 3/2014 | Fossel |
| 2014/0072618 A1 | 3/2014 | Fossel |
| 2014/0073697 A1 | 3/2014 | Fossel |
| 2014/0086980 A1 | 3/2014 | Fossel |
| 2015/0010619 A1 | 1/2015 | Fossel |
| 2015/0011570 A1 | 1/2015 | Fossel |

FOREIGN PATENT DOCUMENTS

| | | | |
|---|---|---|---|
| DE | 10128910 A1 | 12/2002 | |
| EP | 0338291 A1 | 10/1989 | |
| EP | 0391342 A1 | 10/1990 | |
| EP | 0 399 765 A2 | 11/1990 | |
| EP | 0 424 028 A2 | 4/1991 | |
| EP | 1210933 A1 | 6/2002 | |
| FR | 5940 | 10/1966 | |
| FR | 1553063 | 11/1967 | |
| FR | 2602678 | 2/1988 | |
| FR | 2740453 | 4/1997 | |
| FR | 2810540 | 12/2001 | |
| GB | 2094142 A1 | 9/1982 | |
| GB | 2126868 A | 4/1984 | |
| JP | 57-053404 A | 3/1982 | |
| JP | 60-252412 A | 12/1985 | |
| JP | 03-093707 | 4/1991 | |
| JP | 04-005231 | 9/1992 | |
| JP | 05-279250 | * 10/1993 | ............... A61K 9/12 |
| JP | 6-247832 | 9/1994 | |
| JP | 6-287135 A | 10/1994 | |
| JP | 7-53336 | 2/1995 | |
| JP | 07-316075 A | 12/1995 | |
| JP | 09-143098 A | 6/1997 | |
| JP | 9-208460 A | 8/1997 | |
| JP | 9-241156 A | 9/1997 | |
| JP | 10-167953 | 6/1998 | |
| JP | 2000-186028 A | 7/2000 | |
| JP | 2001-288068 A | 10/2001 | |
| JP | 2002-003373 A | 1/2002 | |
| JP | 2003-286129 A | 10/2003 | |
| JP | 2004-059439 A | 2/2004 | |
| JP | 2005-200370 A | 7/2005 | |
| RU | 2212232 C2 | 9/2003 | |
| RU | 2229286 C2 | 5/2004 | |
| WO | WO 88/06034 A1 | 8/1988 | |
| WO | WO 92/08705 | 5/1992 | |
| WO | WO 92/15276 A2 | 9/1992 | |
| WO | WO 94/09750 A1 | 5/1994 | |
| WO | WO 95/13060 | 5/1995 | |
| WO | WO 95/15147 | 6/1995 | |
| WO | WO 95/15147 A1 | 6/1995 | |
| WO | WO 96/08966 A1 | 3/1996 | |
| WO | WO 96/14748 | 5/1996 | |
| WO | WO 96/29988 A1 | 10/1996 | |
| WO | WO 97/10830 A1 | 3/1997 | |
| WO | WO 97/16983 | 5/1997 | |
| WO | WO 97/39760 A1 | 10/1997 | |
| WO | WO 99/13717 A1 | 3/1999 | |
| WO | WO 00/03689 A2 | 1/2000 | |
| WO | WO 00/40215 A1 | 7/2000 | |
| WO | WO 00/54773 A1 | 9/2000 | |
| WO | WO 00/69469 A1 | 11/2000 | |
| WO | WO 01/45713 A1 | 6/2001 | |
| WO | WO 03/049593 A2 | 6/2003 | |
| WO | WO 03/072039 A2 | 9/2003 | |
| WO | WO 03/078437 A1 | 9/2003 | |
| WO | WO 03/080104 A2 | 10/2003 | |
| WO | WO 2005/081964 A2 | 9/2005 | |
| WO | WO 2005/102282 A1 | 11/2005 | |
| WO | WO 2005/102307 A2 | 11/2005 | |
| WO | WO 2006/096360 A1 | 9/2006 | |
| WO | WO 2008/076287 A2 | 6/2008 | |
| WO | WO 2010/151240 A1 | 12/2010 | |

OTHER PUBLICATIONS

Derwent Summary (Acc No. 199-374526).*
BASF Pharma Ingredients and Services, Ibuprofen Technical Information, Apr. 2010 (p. 11).*
Argiolas, A., "Nitric Oxide is a Central Mediator of Penile Erection," *Neuropharmacology*, vol. 33, No. 11, pp. 1339-1344 (1994).
Birder, et al., "Adrenergic and capasaicin evoked nitric oxide release from urothelium and afferent nerves in urinary bladder," *American Journal of Physiology*, vol. 275, pp. F226-F229 (1998). [Abstract only].
Bunker, C.B., et al., "Alterations in scalp blood flow after the epicutaneous application of 3% minoxidil and 0.1% hexyl nicotinate in alopecia," *Correspondence*, pp. 668-669 (1986).
Cooper, et al., "Transdermal Delivery of Drugs," *CRC Press*, vol. II, pp. 57-62 (1987).
De Boer, E.M., et al., "Does Topical Minoxidil Increase Skin Blood Flow?", *Acta Derm Venereol*, vol. 68, pp. 271-274 (1988).
Dietz, N.M., et al., "Is nitric oxide involved in cutaneous vasodilation during body heating in humans?" *J. Appl. Physiol*, vol. 76, No. 5, pp. 2047-2053 (1994).
Garban, H., et al., "Effect of aging on nitric oxide-mediated penile erection in rats," *Am. J. Physiol.*, H467-H475 (1995).
Hwang, T.I., et al., "Evaluation of Vasculogenic Impotence Using Dynamic Penile Washout Test," *J. Formosan Med. Assoc.*, vol. 89, No. 11, pp. 992-996 (1990).
Kirkeby, H.J., et al., "Role of the L-arginine/nitric oxide pathway in relaxation of isolated human penile cavernous tissue and circumflex veins," *Acta Physiol Scand.*, vol. 149, pp. 385-392 (1993).
Klemp, P., et al., "Subcutaneous Blood Flow in Early Male Pattern Baldness," *J. Invest. Dermatol.*, 92, pp. 725-726 (1989).
Laan, E., et al., "Assessment of female sexual arousal: Response specificity and construct validity," *Psychophysiology*, vol. 32, pp. 476-485 (1995).
Mathias, B. J., et al., "Topical Capsaicin for Chronic Neck Pain," *Am. J. Phys. Rehabil.*, vol. 74, pp. 39-44 (1995).
Moody, J.A., et al., "Effects of Long-Term Oral Administration of L-arginine on the Rat Erectile Response," *The Journal of Urology*, vol. 158, pp. 942-947 (1997).
Owen, J.A. et al., "Topical Nitroglycern: A Potential Treatment for Impotence," *The Journal of Urology*, vol. 143, pp. 546-548 (1989).
Pauly, et al., "Liposomes containing amino acids and peptides and proteins for skin care," (1998) [Abstract only].
Riedel, et al., "Different Mechanisms of L-Arginine Induced Dilation of Brain Arterioles in Normotensive and Hypertensive Rats", CA: 122 (11) 130053t [Abstract only].
Singh, S., et al., "Response of digital arteries to endothelium dependent and independent vasodilators in patients with Raynaud's phenomenon," *European Journal of Clinical Investigation*, vol. 25, pp. 182-185 (1995).
Sonntag, M., et al., "Role of nitric oxide in local blood flow control in the anaesthetized dog," *European Journal of Physiology*, pp. 194-199 (1992).
Tseng, L.F., et al., "Increase of nitric oxide production by L-arginine potentiates i.c.v. administered β-endorphin-induced antinociception in the mouse," *European Journal of Pharmacology*, vol. 212, pp. 301-303 (1992).
Wang, R. et al., "Nitric Oxide Mediates Penile Erection in Cats," *The Journal of Urology*, vol. 151, pp. 234-237 (1994).
Whitmore, E.S., et al., "Acute Effect of Topical Minoxidil on Digital Blood Flow in Patients with Raynaud's Phenomenon," *The Journal of Rheumatology*, vol. 22, No. 1, pp. 50-54 (1995).
Hirvonen, J. et al. "Effect of diffusion potential, osmosis and ion-exchange on transdermal drug delivery: theory and experiments", Jornal of Controlled Release 56 (1998) 33-39.
Nakaki, T. et al., "Beneficial Circulatory Effect of L-Arginine," *Jpn. J. Pharmacol.* 66, 167-171 (1994).
The Merck Index, An Encyclopedia of Chemicals, Drugs, and Biologicals, Twelfth Edition, p. 817.

(56) References Cited

OTHER PUBLICATIONS

International Preliminary Report on Patentability for International Application No. PCT/US2005/005726, published Aug. 30, 2006.
International Search Report for International Application No. PCT/US05/13230 published Oct. 28, 2005.
International Search Report for International Application Serial No. PCT/US98/19429, published Jan. 11, 1999.
International Search Report for International Application Serial No. PCT/US05/13228 published Jul. 5, 2005.
Written Opinion for International Application No. PCT/US05/13230 published Oct. 28, 2005.
Written Opinion for International Application No. PCT/US2005/005726 published Aug. 30, 2006.
Written Opinion for International Application Serial No. PCT/US05/13228 published Jul. 5, 2005.
Fossel, Eric T. "Improvement of Temperature and Flow in Feet of Subjects with Diabetes With Use of a Transdermal Preparation of L-Arginine" Diabetes Care, vol. 27, No. 1, Jan. 2004, pp. 284-285.
Haldiya, Kripa Ram, et al. "Dermal Ulcers and Hypertension in Salt Workers" Current Science, vol. 87, No. 8, Oct. 25, 2004, pp. 1139-1141.
Matuszak, Daniel et al. "Thermodynamic Driving Force for Molecular Diffusion—Lattice Density Functional Theory Predictions" J. Non-Equilib. Thermodym. 2006, vol. 31, No. 4, pp. 355-384.
Schölermann, A. et al. "Clinical and biophysical efficacy of a novel coenzyme $Q_{10}$, containing anitwrinkle cream (Eucerin® Q10 active)" J EP Acad Dermatol Venereol, 11: S270, year unknown.
Suhonen, T. Marjukka et al. "Epidermal cell culture model derived from rat keratinocytes with permeability characteristics comparable to human cadaver skin" Euorpean Journal of Pharmaceutical Sciences 20 (2003) 107-113.
Supplementary European Search Report for EP 98946099.3 mailed Mar. 1, 2006.
Extended Europrean Search Report for EP 09014985.7 mailed Apr. 22, 2010.
Writtion Opinion for PCT/US98/19429 mailed Jul. 14, 1999.
International Preliminary Examination Report for PCT/US98/19429 mailed Apr. 6, 2000.
Supplementary European Search Report for EP 05723558.2 mailed Feb. 17, 2009.
International Search Report and Written Opinion for PCT/US05/05726 mailed Sep. 19, 2005.
Supplementary European Search Report for EP 05737763.2 mailed May 12, 2009.
International Preliminary Report on Patentability for PCT/US2005/013228 mailed Nov. 2, 2006.
Supplementary European Search Report for EP 05737752.5 mailed Apr. 21, 2009.
International Preliminary Report on Patentability for PCT/US2005/013230 mailed Nov. 2, 2006.
[No Author Listed] BioSpace Press Release Transdermal Ibuprofen development Complete: NDA to Be Filed (web page) http://biospace.com/news_story.aspx?NewsEntityId=18470820. Published Dec. 16, 2004. 2 pages.
[No Author Listed] MoonDragon's Health & Wellness: Nutrition Basics: Amino Acids—Arginine. Unknown date. 10 pages.
[No Author Listed] Peripheral Vascular Disease—Wikipedia (web page) http://en.wikipedia.org/wiki/Peripheral_vascular_disease [Jan. 18, 2010]. 5 pages.
[No Author Listed] Peripheral Vascular Disease (web page) http://www.americanheart.org/presenter.jhtml?identifier=4692 [Jan. 18, 2010]. 2 pages.
[No Author Listed] Sex and Sexuality Orgasm Information. Extended Orgasm. Unknown date. 7 pages.
[No Author Listed] "Xanthan gum." Wikipedia. Available at.http://en.wikipedia.org/wiki/Xanthan. Last accessed Apr. 13, 2009. 3 pages.
[No Author Listed] "Xanthan gum used in cosmetic products." Dermaxime: bio-cellular skin.products. Available at http://www.dermaxime.com/xanthan.htm. Last accessed Apr. 23, 2009. 4 pages.
Goldenberg, The Care of the Diabetic Foot. Judy Dan Research & Treatment Centre. Available at http://www.ontariowoundcare.com/footcarephysician.htm. Last accessed Sep. 20, 2010. 9 pages.
Hirsch et al., Peripheral Arterial Disease Detection, Awareness, and Treatment in Primary Care. J Am Med Assoc. 2001;286(11):1317-1324.
McLatchie et al., The effects of pH on the interaction between capsaicin and the vanilloid receptor in rat dorsal root ganglia neurons. Br J Pharmacol. Feb. 2001;132(4):899-908.
Scholermann et al., Clinical and biophysical efficacy of a novel body cream (Eucerin® amino body cream) for aged dry skin containing urea and L-arginine. J Euro Acad Dermatol Venereol. 1998; 11:S270. Abstract P363.
Shukla et al., Nitric oxide inhibits wounds collagen synthesis. Mol Cell Biochem. Oct. 1999;200(1-2):27-33.
Thompson, Part IV. Exercise as Adjunctive Therapy for Patients with Vascular Disease. Definition and Classification of Peripheral Arterial Disease. In: Exercise & Sports Cardiology. 2001: 372.
International Search Report and Written Opinion for International Application No. PCT/US2009/003750 mailed May 19, 2010.
International Search Report and Written Opinion for International Application No. PCT/US2009/003749 mailed May 19, 2010.
Extended European Search Report for EP 11173316.8 mailed Sep. 22, 2011.
Extended European Search Report for EP 11182318.3 mailed Jan. 20, 2012.
Extended European Search Report for EP 11174380.3 mailed Jan. 13, 2012.
Extended European Search Report for EP 11174375.3 mailed Jan. 13, 2012.
International Preliminary Report on Patentability for PCT/US2009/003750 mailed Jan. 12, 2012.
International Preliminary Report on Patentability for PCT/US2009/003749 mailed Jan. 12, 2012.
Boger et al., Restoring vascular nitric oxide formation by L-arginine improves the symptoms of intermittent claudication in patients with peripheral arterial occlusive disease. J Am Coll Cardiol. Nov. 1998;32(5):1336-44.
International Search Report and Written Opinion for PCT/US2011/067993 mailed May 1, 2012.
International Search Report and Written Opinion for PCT/US2011/067987 mailed Apr. 30, 2012.
International Search Report and Written Opinion for PCT/US2011/067991 mailed Apr. 30, 2012.
International Search Report and Written Opinion for PCT/US2011/067992 mailed Apr. 30, 2012.
International Search Report and Written Opinion for PCT/US2011/067990 mailed Apr. 30, 2012.
Biagini et al., [Intermittent claudication: topical treatment with isosorbide dinitrate ointment. Preliminary results]. G Ital Cardiol. 1981;11(7):514-521.
Gutman et al., Molecular discovery of transdermal delivery nanotechnology from computer experiments and experimental R & D. Strategic Science Technologies. Presented at the Langer USA-Japan Drug Delivery Conference. Maui, Hawaii. Dec. 2011. 21 pgs.
Flick, Cosmetics Additives: An Industrial Guide. Noyes Publications, Park Ridge, New Jersey, U.S.A. 1991: 790. (the year of publication is sufficiently earlier than the effective U.S. filing date and any foreign priority date so that the particular month of publication is not in issue. See MPEP 609.04(a)).
Katzbauer, Properties and applications of xanthan gum. Polymer Degradation and Stability. 1998;59(1-3): 81-4.
Napoli et al., Nitric oxide-releasing drugs. Annu Rev Pharmacol Toxicol. 2003;43:97-123. Epub Jan. 10, 2002.
Singh, Xantham Gum. Printed from: Pharmaceutical Excipients. London: Pharmaceutical Press. 2006. Electronic version. Last revision Aug. 7, 2005. 6 pages.
Tiso et al., Oral versus topical ibuprofen for chronic knee pain: A prospective randomized pilot study. Pain Physician. Sep./Oct. 2010;13:457-467.
Yasuda, The role of nitric oxide in the pathophysiology of diabetic neuropathy. The Autonomic Nervous System. 2003;40:285-289.

(56) References Cited

OTHER PUBLICATIONS

Bessatsu, Igaku no Ayumi, Shinkei Shikkan (A Separate Volume: Progress in Medicine, Neurological Desiases), 1999:314-6. Chinese.
Rinshyo, Treatment and prevention of diabetic foot ulcer. Shin Jidai no Tonyobyogaku (Studies on Diabetes in a New Age). 2002;4:354-8. Chinese.
International Preliminary Report on Patentability for PCT/US2011/067993 mailed Jul. 11, 2013.
International Preliminary Report on Patentability for PCT/US2011/067987 mailed Jul. 11, 2013.
International Preliminary Report on Patentability for PCT/US2011/067991 mailed Jul. 11, 2013.
International Preliminary Report on Patentability for PCT/US2011/067992 mailed Jul. 11, 2013.
International Preliminary Report on Patentability for PCT/US2011/067990 mailed Jul. 11, 2013.
Extended European Search Report for EP 13167916.9 mailed Jul. 30, 2013.
Japanese Office Action for Application No. 2011-93358 mailed Nov. 1, 2012.
Hyldahl et al., Effects of ibuprofen topical gel on muscle soreness. Med Sci Sports Exerc. Mar. 2010;42(3):614-21.
Lin et al., Efficacy of topical non-steroidal anti-inflammatory drugs in the treatment of osteoarthritis: meta-analysis of randomised controlled trials. BMJ. Aug. 7, 2004;329(7461):324. Epub Jul. 30, 2004.
Trnavskýet al., Efficacy and safety of 5% ibuprofen cream treatment in knee steoarthritis. Results of a randomized, double-blind, placebo-controlled study. J Rheumatol. Mar. 2004;31(3):565-72.
Whitefield et al., Comparative efficacy of a proprietary topical ibuprofen gel and oral ibuprofen in acute soft tissue injuries: a randomized, double-blind study. J Clin Pharm Ther. Dec. 2002;27(6):409-17.
Extended European Search Report for EP 11852275.4 mailed Dec. 9, 2014.
Extended European Search Report for EP 11854321.4 mailed Dec. 8, 2014.
Extended European Search Report for EP 11853771.1 mailed Dec. 11, 2014.
Extended European Search Report for EP 11853913.9 mailed Dec. 5, 2014.
Extended European Search Report for EP 11854161.4 mailed Dec. 9, 2014.
Sauermann et al., Caplus Copyright. AN 1995: 648333, abstracting WO 9515147, Jul. 1995.

\* cited by examiner

TRANSDERMAL DELIVERY OF BENEFICIAL SUBSTANCES EFFECTED BY A HOSTILE BIOPHYSICAL ENVIRONMENT

RELATED APPLICATIONS

This application is a national stage filing under 35 U.S.C. §371 of International Patent Application Serial No. PCT/US2005/013228, filed Apr. 19, 2005, which claims the benefit of U.S. Provisional Patent Application Ser. No. 60/563,573, filed Apr. 19, 2004, entitled "Flow Assisted Transdermal Preparations of Ephedra and Ephedra Components to Avoid Adverse Effects," by E. T. Fossel; U.S. Provisional Patent Application Ser. No. 60/563,575, filed Apr. 19, 2004, entitled "Flow Assisted Transdermal Delivery of Anabolic Steroids," by E. T. Fossel; U.S. Provisional Patent Application Ser. No. 60/563,574, filed Apr. 19, 2004, entitled "Augmented Flow Assisted Transdermal Delivery of Anabolic Steroids," by E. T. Fossel; U.S. Provisional Patent Application Ser. No. 60/563,558, filed Apr. 19, 2004, entitled "Flow Assisted Topical Transdermal Methods of Drug Delivery," by E. T. Fossel; U.S. Provisional Patent Application Ser. No. 60/563,559, filed Apr. 19, 2004, entitled "Transdermal Delivery of Pharmaceutical Agents Effected by a Hostile Biophysical Environment," by E. T. Fossel; U.S. Provisional Patent Application Ser. No. 60/563,560, filed Apr. 19, 2004, entitled "Transdermal Drug Delivery by Means of a High Ionic Strength Environment," by E. T. Fossel; U.S. Provisional Patent Application Ser. No. 60/563,576, filed Apr. 19, 2004, entitled "Transdermal Delivery of Ephedra and Ephedra Components by Use of A Hostile Biophysical Environment," by E. T. Fossel; U.S. Provisional Patent Application Ser. No. 60/563,572, filed Apr. 19, 2004, entitled "An Augmented Flow Assisted Preparation to Increase Muscle Size and Performance," by E. T. Fossel; U.S. Provisional Patent Application Ser. No. 60/563,564, filed Apr. 19, 2004, entitled "A Flow Assisted Preparation to Increase Muscle Size and Performance," by E. T. Fossel; U.S. Provisional Patent Application Ser. No. 60/563,570, filed Apr. 19, 2004, entitled "Transdermal Preparations to Improve Muscle Function and Size," by E. T. Fossel; U.S. Provisional Patent Application Ser. No. 60/563,561, filed Apr. 19, 2004, entitled "Use of a Silicon Based Matrix for Transdermal Delivery of L-Arginine and Adjuncts to Cause Beneficial Effects," by E. T. Fossel; U.S. Provisional Patent Application Ser. No. 60/563,562, filed Apr. 19, 2004, entitled "Transdermal Preparation of Ibuprofen to Reduce Pain and Inflammation," by E. T. Fossel; U.S. Provisional Patent Application Ser. No. 60/563,567, filed Apr. 19, 2004, entitled "A Transdermal Augmented L-Arginine Preparation for Treatment of Headache," by E. T. Fossel; U.S. Provisional Patent Application Ser. No. 60/563,552, filed Apr. 19, 2004, entitled "Flow Assisted Topical Transdermal Method of Drug Delivery of Drugs with Systemic Toxicity," by E. T. Fossel; U.S. Provisional Patent Application Ser. No. 60/563,569, filed Apr. 19, 2004, entitled "Transdermal Delivery of Systematically Toxic Pharmaceutical Agents Effected by a Hostile Biophysical Environment," by E. T. Fossel; and U.S. Provisional Patent Application Ser. No. 60/563,571, filed Apr. 19, 2004, entitled "Transdermal Flow Assisted Localized Delivery of Chemotherapeutic Agents," by E. T. Fossel.

This application also claims the benefit of U.S. Provisional Patent Application Ser. No. 60/563,563, filed Apr. 19, 2004, entitled "Use of Transdermal L-Arginine and Adjuncts to Cause Beneficial Effects by Increasing Local Blood Flow," by E. T. Fossel; U.S. Provisional Patent Application Ser. No. 60/563,565, filed Apr. 19, 2004, entitled "Use of Arginine and Arginine Derivatives and Adjuncts to Improve Grafting of Real and Artificial Skin," by E. T. Fossel; U.S. Provisional Patent Application Ser. No. 60/563,566, filed Apr. 19, 2004, entitled "Transdermal Delivery of L-Arginine for the Purpose of Enhancing the Appearance of the Female Breast," by E. T. Fossel; U.S. Provisional Patent Application Ser. No. 60/563,553, filed Apr. 19, 2004, entitled "Use of A Transdermal L-Arginine and Adjuncts to Improve Bone Healing," by E. T. Fossel; U.S. Provisional Patent Application Ser. No. 60/563,554, filed Apr. 19, 2004, entitled "Use of a Transdermal Preparation of L-Arginine and Adjuncts to Effect Wound Healing," by E. T. Fossel; U.S. Provisional Patent Application Ser. No. 60/563,555, filed Apr. 19, 2004, entitled "Use of a Transdermal Preparation of L-Arginine and Adjuncts to Facilitate Healing of Infection," by E. T. Fossel; U.S. Provisional Patent Application Ser. No. 60/563,556, filed Apr. 19, 2004, entitled "Transdermal Delivery of L-Arginine Preparation to Regress Neuropathy and Heal and Prevent Ulcers," by E. T. Fossel; U.S. Provisional Patent Application Ser. No. 60/563,557, filed Apr. 19, 2004, entitled "A Transdermal Preparation of L-Arginine to Improve Flow in Peripheral Artery Disease and Prevent Claudication," by E. T. Fossel; and U.S. Provisional Patent Application Ser. No. 60/563,551, filed Apr. 19, 2004, entitled "Use of a Transdermal L-Arginine Preparation and Adjuncts to Improve Outcome in Transplant and Plastic Surgery," by E. T. Fossel.

Each of the above applications is incorporated herein by reference.

FIELD OF INVENTION

The present invention generally relates to the transdermal delivery of substances.

BACKGROUND

Local transdermal delivery of drugs, while desirable, is limited by current technologies. Few pharmaceutical entities have successfully been delivered transdermally in effective dosages. For example, a limited number of drugs, such as steroids, nicotine and nitroglycerine, which are non-charged and do not form hydrogen bonds, have been successfully delivered by passive diffusion, relying on the concentration gradient between outside and inside the skin to deliver the agent in accordance with Fick's first law of diffusion. The amount of pharmaceutical agent that can be delivered through simple diffusion is also limited. For instance, once the concentration inside the stratum corneum becomes equal to that outside, flow of pharmaceutical agent may stop. Thus, improvements in the transdermal delivery of substances, locally or systemically, are needed.

SUMMARY OF THE INVENTION

The present invention generally relates to the transdermal delivery of substances, locally or systemically, and in some embodiments, to the transdermal delivery of beneficial substances by a hostile biophysical environment. The subject matter of the present invention involves, in some cases, interrelated products, alternative solutions to a particular problem, and/or a plurality of different uses of one or more systems and/or articles.

This invention relates, in one aspect, to the field of localized transdermal delivery of substances which have a beneficial effect, for example, to the transdermal delivery of herbs, vitamins, minerals, pharmaceutical agents, drugs, peptides, dietary supplements, or other substances affected by a hostile biophysical environment. The hostile biophysical environment may comprise a high ionic strength vehicle in some embodiments, and delivery may be enhanced, in certain cases, by various techniques to increase local blood flow at the delivery site. For instance, substances with localized action may avoid systemic toxicity if delivered locally and transdermally. In some cases, various beneficial substances which function at local sites, rather than systemically, may be more efficaciously administered by transdermal rather than systemic administration. If the beneficial substance is delivered through the skin, a higher dose in the tissue to be treated may be achieved. In addition, a substantially lower total body dose may be achieved in some cases. This can be understood if one considers the non-limiting example of treating pain in finger joints with a NSAID (a nonsteroidal anti-inflammatory drug). If the pain is to be treated systemically, e.g., by oral administration, the whole body, including the finger joints, is dosed with the NSAID. The concentration of NSAID is approximately the same throughout the body, including the finger joints. If, on the other hand, one were to apply the NSAID transdermally to the finger joints, the rest of the body would not be dosed (or would be dosed to a significantly lesser extent). Thus, the total dose of transdermal NSAID would only be a fraction of the dosage required for systemic administration.

In some embodiments, the beneficial substances delivered transdermally may improve health, improve body function, or treat a variety of disease states.

In one set of embodiments, the invention relates to the field of headache treatment, and in some cases, to the use of arginine and/or arginine derivatives or adjuncts to provide effective headache relief. This invention also relates, in another set of embodiments, to the field of relief of pain and/or inflammation and in some cases, to a transdermal preparation of ibuprofen to reduce pain and/or inflammation. In certain instances, the ibuprofen is delivered from a vehicle into the tissue through the use of a hostile biophysical environment.

This invention also relates, in yet another set of embodiments, to systems and methods for improving uptake of muscle improving agents, for example, by increasing local blood flow by delivering a nitric oxide donor such as L-arginine, either alone or with an adjunct such as theophylline. This invention also relates, in still another set of embodiments, to topical methods of administrating anabolic steroids, for example, steroids that exhibit unacceptable systemic toxicity. The steroids may also promote improved muscle size and function through the use of enhanced blood flow.

This invention relates, in one set of embodiments, to topical methods of administering chemotherapeutic or antiviral agents, for instance, to promote healing or recovery, or to prevent recurrence of a localized cancer or viral infection.

In yet another set of embodiments, this invention relates to the field of enhanced sexual function. In some cases, arginine and/or arginine derivatives and adjuncts may be applied to increase genital blood flow, which may increase sexual function.

In one aspect, the invention is a method. The method includes, in one set of embodiments, an act of applying, to a portion of the skin of a subject, a delivery vehicle comprising a pharmaceutical agent in a hostile biophysical environment.

In another aspect, the invention includes a delivery vehicle. In one set of embodiments, the delivery vehicle includes a nitric oxide donor, and a pharmaceutical agent at a dosage effective to treat a localized medical condition, wherein the dosage is lower than the effective dosage of the pharmaceutical agent when taken orally. In another set of embodiments, the delivery vehicle includes a nitric oxide donor, and a pharmaceutical agent able to treat one or more medical conditions selected from the group consisting of cramps, pain, migraine, arthritis, swelling, sexual dysfunction, hair loss, skin ulcers, and migraine.

One aspect of the invention is directed to a method comprising an act of administering, to a subject, a delivery vehicle comprising a nitric oxide donor contained within a hostile biophysical environment. Another aspect of the invention is directed to an article comprising a cream containing a nitric oxide donor in a hostile biophysical environment.

Several methods are disclosed herein of administering a subject (which may be human or a non-human animal) with a composition for prevention or treatment of a particular condition. It is to be understood that in each such aspect of the invention, the invention specifically includes, also, the composition for use in the treatment or prevention of that particular condition, as well as use of the composition for the manufacture of a medicament for the treatment or prevention of that particular condition.

The present invention, in another aspect, is directed to a method of making one or more of the embodiments described herein. In yet another aspect, the present invention is directed to a method of using one or more of the embodiments described herein. In still another aspect, the present invention is directed to a method of promoting one or more of the embodiments described herein.

Other advantages and novel features of the present invention will become apparent from the following detailed description of various non-limiting embodiments of the invention. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

DETAILED DESCRIPTION

The present invention generally relates to the transdermal delivery of substances and, in some embodiments, to the transdermal delivery of beneficial substances by a hostile biophysical environment. In one aspect, various methods for the transdermal delivery of beneficial substances are disclosed. By creating a hostile biophysical environment, beneficial substances may be delivered, according to certain embodiments, through the stratum corneum of the skin into the body. Beneficial substances include, but are not limited to, pharmaceutical agents, drugs, vitamins, co-factors, peptides, dietary supplements, and others. The beneficial effects disclosed include, for instance, relief of pain and inflammation, prevention and healing of ulcers of the skin, relief of headache, improved sexual function and enjoyment, growth of hair on the scalp, improving muscle size and/or function, removing body fat and/or cellulite, treating cancer, treating viral infections and others. A hostile biophysical environment may also be used in conjunction with systems and methods for increasing local blood flow, according to one set of embodiments. For example, by using a nitric oxide donor such as L-arginine, local blood flow may be increased, e.g., by transdermally delivering the nitric oxide precursor. The nitric oxide donor may be the sole cause of increased blood flow, or it may be supplemented with an adjunct such as theophylline.

The following documents are incorporated herein by reference: U.S. Provisional Patent Application Ser. Nos. 60/563, 563, 60/563,558, 60/563,559, 60/563,560, 60/563,561, 60/563,562, 60/563,572, 60/563,564, 60/563,565, 60/563, 566, 60/563,567, 60/563,553, 60/563,554, 60/563,555, 60/563,556, 60/563,557, 60/563,551, 60/563,552, 60/563,569, 60/563,570, 60/563,571, 60/563,573, 60/563,574, 60/563,575, and 60/563,576, each filed Apr. 19, 2004, by E. T. Fossel; U.S. Provisional Patent Application Ser. No. 60/546,214, filed Feb. 23, 2004, entitled "Topical Delivery of a Nitric Oxide Donor to Improve Body and Skin Appearance," by E. T. Fossel; U.S. patent application Ser. No. 08/932,227, filed Sep. 17, 1997, entitled "Topical Delivery of Arginine of Cause Beneficial Effects," by E. T. Fossel, published as 2002/0041903 on Apr. 11, 2002; U.S. patent application Ser. No. 10/201,635, filed Jul. 22, 2002, entitled "Topical Delivery of L-Arginine to Cause Beneficial Effects," by E. T. Fossel, published as 2003/0028169 on Feb. 6, 2003; U.S. patent application Ser. No. 10/213,286, filed Aug. 5, 2002, entitled "Topical and Oral Arginine to Cause Beneficial Effects," by E. T. Fossel, published as 2003/0018076 on Jan. 23, 2003; International Patent Application No. PCT/US98/19429, filed Sep. 17, 1998, entitled "A Delivery of Arginine to Cause Beneficial Effects," by E. T. Fossel, published as WO 99/13717 on Mar. 25, 1999; U.S. Pat. No. 5,895,658, issued Apr. 20, 1999, entitled "Topical Delivery of L-Arginine to Cause Tissue Warming," by E. T. Fossel; U.S. Pat. No. 5,922,332, issued Jul. 13, 1999, entitled "Topical Delivery of Arginine to Overcome Pain," by E. T. Fossel; U.S. Pat. No. 6,207,713, issued Mar. 27, 2001, entitled "Topical and Oral Delivery of Arginine to Cause Beneficial Effects," by E. T. Fossel; U.S. Pat. No. 6,458,841, issued Oct. 1, 2002, entitled "Topical and Oral Delivery of Arginine to Cause Beneficial Effects," by E. T. Fossel; International Patent Application No. PCT/US2005/005726, filed Feb. 23, 2005, entitled "Topical Delivery of a Nitric Oxide Donor to Improve Body and Skin Appearance," by E. T. Fossel; and an international patent application filed on even date herewith, entitled "Use of Transdermal L-Arginine and Adjuncts to Cause Beneficial Effects by Increasing Local Blood Flow," by E. T. Fossel.

Detailed descriptions of the various embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure, or manner.

One aspect of the invention provides for the delivery of beneficial substances such as pharmaceutical agents (e.g., drugs, biological compounds, etc.) into the body, and such treatments may be systemic or localized, e.g., directed to a specific location of the body, such as the head, one or more specific muscles, the genitals, etc., depending on the specific application.

In one set of embodiments, pharmaceutical agents are introduced to aid in treatment of medical conditions or diseases, and the symptoms associated thereof. In some embodiments, the invention provides for the treatment of medical conditions or diseases and/or ailments using pharmaceutical agents (for example, to treat a subject diagnosed with a medical condition or disease, as described herein), and in some cases, the invention provides for the delivery of a minimum amount of pharmaceutical agents to provide effective levels of medication to an effected area topically while limiting side effects. In some cases, the effective dosage of the pharmaceutical agent may be lower than the effective dosage of the pharmaceutical agent when taken orally. Other embodiments of the invention provides methods for treating cancer, viral infections, erectile dysfunction, sexual dysfunction, an ulcer, swelling, or arthritis. Still another embodiment of the invention provides methods for treating pain, for example, pain from migraine, other headaches, joint pain, muscle pain and other types of pain, Yet another embodiment of the present invention provides methods for restoring hair growth, for example, on a portion of the scalp, which may be scarce in hair.

Non-limiting examples of pharmaceutical agents include small molecules (e.g., having a molecular weight of less than about 2,000 Da, less than about 1,500 Da, or less than about 1,000 Da), peptides (e.g., having less than about 10, less than about 15, less than about 20, or less than about 25 amino acids), proteins (typically larger than peptides), hormones, vitamins, nucleic acids, or the like. Additional examples of suitable pharmaceutical agents for use with the present invention include, but are not limited to, NSAIDs (nonsteroidal anti-inflammatory drugs) such as acetylsalicylsalicylic acid, naproxen, celecoxib, refecoxib, etc.; pharmaceutical agents with narcotic action such as morphine, codine, propoxyphene, oxycodone, hydrocodon, or other similar narcotics; pharmaceutical agents for erectile or sexual dysfunction such as yohimbie, alprostadil, sildenafil, cialis, uprima, vardenaifl, or the like; pharmaceutical agents for migraine such as dihydroergotamine and its salts, ergotamine and its salts, surnatripan and its salts, rizatriptan and its salts, zolmitriptan and its salts, etc.; pharmaceutical agents for hair treatment such as finasteride, eflornithine, minoxidil, or the like; or other pharmaceutical agents such as niacin, lidocaine, benzocaine, ibuprofen, etc. Additional examples include muscle improving agents, for example, creatine or creatine precursors (e.g., creatine phosphate), arginine and/or other nitric oxide donors, and/or ATP precursors such as, inosine, adenosine, inosine, adenine, hypoxanthine, ribose, phosphate (e.g., monosodium phosphate), etc., and/or anabolic steroid agents, such as androstene, DHEA, androstenediol, androstenedione, or the like. Another example is ephedra or its components, such as ephedrine and pseudoephedrine. Yet another example are chemotherapeutic agents or agents for treating cancer and/or viral infections, for example, but not limited to tamoxifen (e.g., for breast cancer treatment), cis-platin, carboplatin and related molecules, chclophosphamide and related molecules, vinca alkaloids, epipodophyllotoxins including taxol, acyclovir, or the like. For example, the cancer and/or viral infections may be skin cancer, breast cancer, penile cancer, testicular cancer, or other localized cancers, or viral infections, such as herpes.

As a particular, non-limiting example, ibuprofen is an effective agent against pain when orally administered. However, it is irritating to the lining of the stomach, and people with a tendency to develop ulcers or have an irritated upper gastrointestinal track are typically warned to avoid the use of ibuprofen. The present invention thus allows the topical application of ibuprofen to the site of inflammation or pain, while avoiding the rest of the body, especially the stomach.

As another particular, non-limiting example, while growth hormones, steroids, supplements, and other such agents have been administered orally and by injection to improve muscle size and function, these muscle improving agents are often distributed throughout the body, resulting in only a small portion of the agent acting at the muscle area being used and developed. Muscle requires both creatine phosphate (CrP) and adenosine triphosphate (ATP) to function. Often muscle has insufficient amounts of these substances and their precursors to maintain high level function. Administration of these substances and their precursors have been attempted but in low dose that is ineffective and in high dose is both very expensive and produces side effects such as gastrointestinal distress. Use of topical transdermal delivery to the desired muscle or muscles of a muscle improving agent, according to various embodiments, may localize the dose to the desired area, and potentially results in a higher concentration of the agent at the desired area.

A variety of methods for effecting or improving absorption of beneficial substances (including pharmaceutical agents) are also included in various aspects of the invention. In some cases, a hostile biophysical environment may be used. In a hostile biophysical environment, the environment surrounding the beneficial substance may be such that the beneficial substance is a chemically/energetically unfavorable environment, relative to the skin (e.g., the chemical potential and/or the free energy of the beneficial substance within the hostile biophysical environment is significantly greater than the chemical potential and/or the free energy of the beneficial substance within the skin, thus energetically favoring transport into the skin), especially the stratum corneum. The hostile biophysical environment which raises the chemical potential and/or the free energy of the beneficial substance can be comprised of a high ionic strength, a high concentration of osmotic agents such as ureas, sugars, or carbohydrates, a high pH environment (e.g., greater than about 9, greater than about 10, greater than about 11, greater than about 12, or greater than about 13), a low pH environment (less than about 5, less than about 4, less than about 3 or less than about 2), highly hydrophobic components, or highly hydrophilic components or other substances that cause an increase in the chemical potential and/or free energy of the beneficial substance. A hydrophobic component may have an octanol-water partition coefficient of at least about 100, at least about 1000, at least about $10^4$, at least about $10^5$, or more in some cases. Similarly, a hydrophilic component may have an octanol-water partition coefficient of less than about 0.01, less than about $10^{-3}$, less than about $10^{-4}$, or less than about $10^{-5}$ in some cases.

In some cases, the delivery vehicle defines the biophysical hostile environment. In other cases, the beneficial substance may be packaged in such a way that it is carried into tissue and/or its charge is neutralized by derivitization and/or by forming a neutral salt. Examples of biophysically hostile environments include, but are not limited to, high ionic strength environments (e.g., by the addition of ureas, sugars, carbohydrates, and/or ionic salts such as lithium chloride, sodium chloride, potassium chloride, calcium chloride, magnesium chloride, choline chloride, sodium fluoride, lithium bromide, etc., as well as combinations of these and/or other agents, for instance at high ionic strengths (for example, greater than about 0.25 M, greater than about 1 M, greater than about 2 M, greater than about 3 M, greater than about 5 M, greater than about 10 M, greater than about 15 M, greater than about 20 M, greater than about 25 M, etc., or in some cases, between about 0.25 M and about 15 M, between about 5 M and about 15 M, between about 10 M and about 15 M, etc.); high or low pH environments (e.g., by adding pharmaceutically acceptable acids or bases, for example, such that the pH is between about 3 and about 7, between about 3 and about 6, between about 3 and about 5, between about 7 and about 11, between about 8 and about 11, between about 9 and about 11, etc.); or highly hydrophobic environments (e.g., by decreasing water content and increasing lipid, oil and/or wax content of the environment). Other highly charged molecules such as polylysine, polyglutamine, polyaspartate, etc., or copolymers of such highly charged amino acids may also be used in certain embodiments to create the hostile biophysical environment. Non-limiting examples of packaging which would be carried into tissue includes liposomes or emulsions of collagen, collagen peptides or other components of skin or basement membrane. Non-limiting examples of neutralization of charge include delivery of the beneficial substance in the form or an ester or salt which is electronically neutral. In some embodiments, the hostile biophysical environment may include any two or more of these conditions. For instance, the hostile biophysical environment may include high ionic strength and a high pH or a low pH, a highly hydrophobic environment and a high pH or a low pH, a highly hydrophobic environment that includes liposomes, or the like.

A hostile biophysical environment may also be created in some embodiments by placing a beneficial substance that is relatively highly charged into a hydrophobic, oily environment such as in an oil-based cream or lotion containing little or no water. Absorption may further be aided by combining the use of hostile biophysical environments with the use of penetrating agents, as further described below.

It should be noted that a hostile biophysical environment optimized for one beneficial substance may not necessarily be optimal for another beneficial substance. For example, an optimal hostile biophysical environment for a beneficial substance that is non-charged and does not form hydrogen bonds, in one embodiment of the invention, may not necessarily be optimal for other embodiments of the invention, in which a beneficial substance is charged, and/or in embodiments in which the beneficial substance is able to form hydrogen bonds. Thus, different hostile biophysical environment(s) may be prepared or optimized for different application(s) including different beneficial substance(s) being delivered using the hostile biophysical environment(s).

In certain aspects of the invention, a pharmaceutical agent or other beneficial substance may be combined with a penetrating agent, i.e., an agent that increases transport of the pharmaceutical agent or other beneficial substance into the skin, relative to transport in the absence of the pharmaceutical agent or other beneficial substance. In some embodiments, the penetrating agent may be combined with a hostile biophysical environment. Examples of penetrating agents include oleoresin capsicum or its constituents, or certain molecules containing heterocyclic rings to which are attached hydrocarbon chains.

Non-limiting examples of penetrating agents include, but are not limited to, cationic, anionic, or nonionic surfactants (e.g., sodium dodecyl sulfate, polyoxamers, etc.); fatty acids and alcohols (e.g., ethanol, oleic acid, lauric acid, liposomes, etc.); anticholinergic agents (e.g., benzilonium bromide, oxyphenonium bromide); alkanones (e.g., n-heptane); amides (e.g., urea, N,N-dimethyl-m-toluamide); fatty acid esters (e.g., n-butyrate); organic acids (e.g., citric acid); polyols (e.g., ethylene glycol, glycerol); sulfoxides (e.g., dimethylsulfoxide); terpenes (e.g., cyclohexene); ureas; sugars; carbohydrates or other agents. In one embodiment, the penetrating agent includes a salt, e.g., as previously described.

The present invention, in one aspect, provides various systems and techniques for increasing local blood flow. For example, increased blood flow may be used to introduce pharmaceutical agents (e.g., drugs, biological compounds, etc.) to aid in treatment of medical conditions or diseases and the symptoms associated thereof (for example, to treat a subject diagnosed with a medical condition or disease, as described herein), and/or the increased blood flow may be used to provide effective treatment of medical conditions or diseases and/or ailments with the minimum amount of pharmaceutical agents possible to provide effective levels of medication to an effected area topically while limiting side effects. In one set of embodiments, a nitric oxide donor such as L-arginine and/or L-arginine hydrochloride in an effective concentration may be used to increase localized blood flow, which may enhance delivery of a pharmaceutical agent or other beneficial substance, e.g., to locally afflicted tissue. Nitric oxide may relax the blood vessels, allowing for increased blood flow. In some cases, one or more nitric oxide donors (e.g., 2, 3, 4, 5, 6, 7, 8, 9, 10, etc. nitric oxide donors) may be combined with one or more beneficial substances (e.g., 2, 3, 4, 5, 6, 7, 8, 9, 10, etc. beneficial substances) in a suitable hostile biophysical environment, as described herein.

Besides L-arginine and L-arginine hydrochloride, other non-limiting examples of nitric oxide donors include D,L-arginine, D-arginine, or alkyl (e.g., ethyl, methyl, propyl, isopropyl, butyl, isobutyl, tert-butyl, etc.) esters of L-arginine and/or D-arginine (e.g., a methyl ester, an ethyl ester, a propyl ester, a butyl ester, etc.) and/or salts thereof, as well as other derivatives of arginine and other nitric oxide donors. For instance, non-limiting examples of pharmaceutically acceptable salts include hydrochloride, glutamate, butyrate, or glycolate (e.g., resulting in L-arginine glutamate, L-arginine butyrate, L-arginine glycolate, D-arginine hydrochloride, D-arginine glutamate, etc.). Other examples of nitric oxide donors include L-arginine-based compounds such as, but not limited to, L-homoarginine, N-hydroxy-L-arginine, nitrosylated L-arginine, nitrosylated L-arginine, nitrosylated N-hydroxy-L-arginine, nitrosylated N-hydroxy-L-arginine, citrulline, ornithine, linsidomine, nipride, glutamine, etc., and salts thereof (e.g., hydrochloride, glutamate, butyrate, glycolate, etc.). Still other non-limiting examples of nitric oxide donors include S-nitrosothiols, nitrites, 2-hydroxy-2-nitrosohydrazines, or substrates of various forms of nitric oxide synthase. In some cases, the nitric oxide may be a compound that stimulates endogenous production of nitric oxide in vivo. Examples of such compounds include, but are not limited to, L-arginine, substrates of various forms of nitric oxide synthase, certain cytokines, adenosine, bradykinin, calreticulin, bisacodyl, phenolphthalein, OH-arginine, or endothelein.

It should be understood that, in any of the embodiments described herein that describe L-arginine, other nitric oxide donors may also be used instead, or in combination with, L-arginine, in other embodiments of the invention.

Without wishing to be bound to any theory, it is generally believed that the flow of the pharmaceutical agent or other beneficial substance across the skin may slow as it builds up within the tissue. Fick's first law of diffusion suggests that when the concentration inside becomes substantially equal to that outside, passive flow stops. The increased local blood flow may prevent or at least decrease the stoppage of the flow of the pharmaceutical agent or other beneficial substance. Thus, when the vehicle containing the pharmaceutical agent or other beneficial substance and a nitric oxide donor, such as L-arginine, is applied to the skin, the pharmaceutical agent or other beneficial substance exits the vehicle into the tissue more readily, as the pharmaceutical agent is dispersed by flow and does not build up in concentration in the tissue. Thus, in certain embodiments, pharmaceutical agents or other beneficial substances may be introduced into the skin, for example, ibuprofen, anabolic steroids, or other agents or substances described herein.

One set of embodiments provides for increased blood flow to the genitals, for example, using a nitric oxide donor such as L-arginine, optionally in combination with a silicon-based transdermal preparation and/or an adjunct such as theophylline. Adequate local genital blood flow is important for optimal sexual function and satisfaction in both men and women. In men it is important to achieve and maintain an erection. In women it is important for nerve sensitivity which is required to attain satisfying orgasms. In some cases, the preparation may be contained within a condom, optionally with other sexual-enhancing agents, such as lubricants.

A non-limiting example of such a preparation includes a silicon-based vehicle (e.g., a vehicle that contains a silicon-containing substance) with properties of excellent absorption into the skin which also contains L-arginine hydrochloride (7.5% w/v), theophylline (5% w/v) and a mixture of high molecular weight polydimethylsiloxane and a low viscosity cyclotetrasiloxane (commercially known as Dow Corning 1411 fluid), and water prepared as an emulsion. The silicon emulsion provides a hostile biophysical environment in this example. The emulsion is applied to the genitals (e.g., the penis, or the clitoris and/or the vagina) and rubbed in until absorbed. The emulsion may facilitate enhanced blood flow to the genitals, bringing oxygen and other nutrients and blood to that tissue. In addition, the silicon may act as a lubricant for improved enjoyment of sexual function. Additional preparations are discussed in more detail herein. Other examples of silicon-containing substances include polydimethylsiloxane, cyclopentasiloxane, dimethicol, or dimethicon. For example, a preparation of the invention may be a cream containing water (20-80%), a polydimethylsiloxane/cyclopentasiloxane mixture (20-90% w/v) and TWEEN 20 (1-10%), and the pH may be between about 3 and about 11.

A "nitric oxide donor," as used herein, is a compound that contains therein a nitric oxide (NO) moiety, where the compound is able to release nitric oxide and/or chemically transfer the nitric oxide moiety to another molecule, directly or indirectly, for example, through a biological process. The nitric oxide donor may release nitric oxide into the skin, and/or tissues such as muscles and/or elements of the circulatory system in close proximity to the surface of the skin. Non-limiting examples of nitric oxide donors include arginine (e.g., L-arginine and/or D-arginine), arginine derivatives (e.g., L-arginine hydrochloride and/or D-arginine hydrochloride), nitroglycerin, polysaccharide-bound nitric oxide-nucleophile adducts, N-nitroso-N-substituted hydroxylamines, 1,3-(nitrooxymethyl)phenyl-2-hydroxybenzoate, etc., as described in more detail herein. In some cases, the concentration of nitric oxide and/or the nitric oxide donor may be tailored to have a duration of effective treatment of at least about 3 hours, at least about 5 hours, or at least about 8 hours or more in certain instances. The duration may also be controlled, for instance, by controlling the concentration of a penetrating agent used in conjunction with nitric oxide and/or the nitric oxide donor. The actual concentration for a particular application can be determined by those of ordinary skill in the art using no more than routine experimentation, for example, by measuring the amount of transport of nitric oxide and/or the nitric oxide donor as a function of concentration in vitro across cadaver skin or suitable animal models, skin grafts, synthetic model membranes, or the like.

As a particular non-limiting example, in one embodiment, nitric oxide is provided using L-arginine, for example, at a concentration of at least about 0.5% by weight (wt % or w/v) of L-arginine (optionally with one or more penetrating agents as discussed herein, for example, a penetrating agent able to create a hostile biophysical environment), at least about 0.75 wt %, at least about 1 wt %, at least about 2 wt %, at least about 3 wt %, at least about 5 wt %, at least about 7 wt %, at least about 10 wt %, or at least about 15 wt %. The L-arginine may be present in a suitable delivery vehicle, such as a cream or a lotion. L-arginine may be particularly useful in some cases due to its low toxicity, its high solubility, or its low cost. Other examples of nitric oxide donors are discussed in International Patent Application No. PCT/US2005/005726, filed Feb. 23, 2005, entitled "Topical Delivery of a Nitric Oxide Donor to Improve Body and Skin Appearance," by E. T. Fossel, incorporated herein by reference.

Thus, another aspect of the invention provides for the delivery of nitric oxide and/or nitric oxide donors into the body, as further described below, and such treatments may be systemic or localized, e.g., directed to a specific location of the body, such as the head, arms, legs, feet, etc., depending on the specific application. The nitric oxide and/or nitric oxide donor may increase local blood flow, thereby enhancing tissue health. Increased blood flow may also assist in the healing process, e.g., where injury or surgery has occurred.

In one set of embodiments, nitric oxide and/or a nitric oxide donor (e.g., arginine and/or an arginine derivative), optionally including an adjunct such as theophylline, may be applied to a subject to improve the outcome of various medical conditions, such as surgical treatments (e.g., at a site of surgery). Non limiting for examples include transplant and plastic surgery, graft sites of real or artificial skin, or other surgically treated areas. In some embodiments of the invention, a treatment of the invention may be applied to improve flow in peripheral artery disease and/or prevent claudication, to improve the circulation in the feet of people with diabetes and others with impaired circulation, to regress neuropathy, to heal or prevent ulcers, to improve bone healing, to treat infection (e.g., bacterial infections, viral infections, fungal infections, etc.), to improve grafting of real or artificial skin, and/or to improve wound healing, and/or to improve a surgically treated area.

In another set of embodiments, nitric oxide and/or a nitric oxide donor (e.g., arginine and/or an arginine derivative), optionally including an adjunct such as theophylline, may be applied to a subject having peripheral artery disease (PAD), for example, in subjects treated invasively or non-invasively. For instance, arteries are often reopened by use of angioplasty, arthectomy or bypass surgery, or through the use of intravenous drug treatments, such as Corlapam, Flolan, or Primacor. Left untreated or unsuccessfully treated, PAD can lead to claudication, which can be incapacitating, resulting not only in great pain but loss of the ability to carry on a normal life. Various systems and methods of the present invention can be used in some cases, as a replacement for and/or in conjunction with such methods of treatment.

Yet another set of embodiments provides for the enhancement of bone healing by increasing local blood flow. Bone healing is a slow and complex process, and it is enhanced by a variety of proteins and cells in the blood. An increase in blood flow rate may thus enhance bone healing. In some cases, the application of a nitric oxide and/or a nitric oxide donor (e.g., arginine and/or an arginine derivative), optionally including an adjunct such as theophylline, may increase blood flow to the bone. Thus, for example, a fractured bone (including a broken bone) may be treated in certain embodiments of the invention.

In still another set of embodiments, an infection may be treated by increasing local blood flow. The body fights infection using cells and cell derived materials found in the blood. Increasing blood flow to the site of an infection can enhance the body's mechanisms for fighting infection. Thus, the application of a nitric oxide and/or a nitric oxide donor (e.g., arginine and/or an arginine derivative), optionally including an adjunct such as theophylline, may increase blood flow to the site of infection, which may promote healing.

Another set of embodiments is generally directed to the treatment of blood flow in persons with diabetes, e.g., in the hands and/or feet. The application of a nitric oxide and/or a nitric oxide donor (e.g., arginine and/or an arginine derivative), optionally including an adjunct such as theophylline, may be used to treat such conditions, thereby increasing blood flow within the hands and/or feet. In some cases, long lasting improvement in blood flow, and/or regression of diabetic neuropathy may be achieved. For example, local blood flow may be increased by at least about 20% or at least about 30%. Still another set of embodiments of the invention are directed to the prevention or treatment of diabetic skin ulcers, e.g., by increasing blood flow, as previously described.

In still another set of embodiments, nitric oxide and/or a nitric oxide donor (e.g., arginine and/or an arginine derivative), optionally including an adjunct such as theophylline, may be applied to the skin, for example, to a skin graft and/or graft material of a skin graft, to a wound in the skin, etc. Often, skin grafts do not have sufficient blood flow, which may lead to graft failure. By enhancing the blood flow to the skin graft, e.g., using the nitric oxide and/or a nitric oxide donor, graft failure may be reduced. In some cases, the nitric oxide and/or nitric oxide donor may be applied to tissues proximate the skin graft, and/or the nitric oxide and/or nitric oxide donor may be induced to migrate to tissues adjacent the skin graft.

Another set of embodiments of the invention is directed to treating medical conditions by not only enhancing blood flow to a treated region of the body, but also by enhancing transdermal delivery of a pharmaceutical agent or other beneficial substance through the use of a nitric oxide and/or a nitric oxide donor (e.g., arginine and/or an arginine derivative), optionally including an adjunct such as theophylline, to increase blood flow at the site of molecular transport. Such embodiments may be relatively simple, inexpensive, and/or non-irritating, and in many cases, no physical or mechanical devices are required. Such transport may be further increased, for example, in combination with penetrating agents or the like, as described herein.

In some aspects of the invention, a nitric oxide and/or nitric oxide donor, and/or a pharmaceutical agent or other beneficial substance, may be administered using a delivery vehicle such as a cream, gel, liquid, lotion, spray, aerosol, or transdermal patch. Examples of delivery vehicles are discussed below. The delivery vehicle may promote transfer into the skin of an effective concentration of the nitric oxide and/or nitric oxide donor, and/or a pharmaceutical agent or other beneficial substance, directly or indirectly. For instance, the delivery vehicle may include one or more penetrating agents, as further described herein. In some embodiments, the delivery vehicle may include a hostile biophysical environment, e.g., using a penetrating agent, etc., as described herein. Those of ordinary skill in the art will know of systems and techniques for incorporating a nitric oxide and/or nitric oxide donor, and/or a pharmaceutical agent or other beneficial substance within delivery vehicles such as a cream, gel, liquid, lotion, spray, aerosol, or transdermal patch. In some cases, the concentration of the nitric oxide and/or nitric oxide donor, and/or a pharmaceutical agent or other beneficial substance in the delivery vehicle can be reduced with the inclusion of a greater amount or concentration of penetrating agent, or increased to lengthen the beneficial effect. In one set of embodiments, the nitric oxide and/or nitric oxide donor, and/or a pharmaceutical agent or other beneficial substance may be used in conjunction with an adjunct, such as theophylline (for example, at 10% weight by volume).

Other materials may be present within the delivery vehicle, for example, buffers, preservatives, surfactants, etc. For instance, the cream may include one or more of water, mineral oil, glyceryl stereate, squalene, propylene glycol stearate, wheat germ oil, glyceryl stearate, isopropyl myristate, steryl stearate, polysorbate 60, propylene glycol, oleic acid, tocopherol acetate, collagen, sorbitan stearate, vitamin A and D, triethanolamine, methylparaben, aloe vera extract, imidazolidinyl urea, propylparaben, PND, or BHA.

As specific non-limiting examples, the cream may have one or more of (w/v): water (20-80%), white oil (3-18%), glyceryl stearate (0.25-12%), squalene (0.25-12%), cetyl alcohol (0.1-11%), propylene glycol stearate (0.1-11%), wheat germ oil (0.1-6%), polysorbate 60 (0.1-5%), propylene glycol (0.05-5%), collagen (0.05-5%), sorbitan stearate (0.05-5%), vitamin A (0.02-4%), vitamin D (0.02-4%), vitamin E (0.02-4%), triethanolamine (0.01-4%), methylparaben (0.01-4%), aloe vera extract (0/01-4%), imidazolidinyl urea (0.01-4%), propylparaben (0.01-4%), BHA (0.01-4%), L-arginine Hydrochloride (0.25-25%), sodium chloride (0.25-25%), magnesium chloride (0.25-25%), and/or choline chloride (0.25-25%). The percentages of each compound can vary (or the compound may be absent in some cases), for example, 1%, 2%, 3%, 4%, 5%, 6%, 7%, 8%, 9%, 10%, 11%, 12%, 13%, 14%, 15%, 20%, etc.

In another embodiment, the cream may include a beneficial substance, such as ibuprofen, and one or more of the following: water (20-80%), L-arginine hydrochloride (0-25%), sodium chloride (0-25%), potassium chloride (0-25%), glyceryl steareate (0-15%), cetyl alcohol (0-15%), squalene (0-15%), isopropyl mysterate (0-15%), oleic acid (0-15%), Tween 20 (0-10%), and/or butanediol (0-10%). The percentages of each compound can vary (or the compound may be absent in some cases), for example, 1%, 2%, 3%, 4%, 5%, 6%, 7%, 8%, 9%, 10%, 11%, 12%, 13%, 14%, 15%, 20%, etc.

In some embodiments, the cream may include a beneficial substance, and one or more ionic salts at a concentration at least sufficient to produce a hostile biophysical environment with respect to the beneficial substance. For example, the cream may include one or more of (w/v): a charged and/or hydrogen bonding beneficial substance with systemic toxicity (0.001-30%), choline chloride (1-30%), sodium chloride (2-30%), and/or magnesium chloride (1-20% w/v). In another example, the cream may include one or more of (w/v): L-arginine hydrochloride (2.5-25%), choline chloride (10-30%), sodium chloride (5-20%), and/or magnesium chloride (5-20%). In still another example, the cream may include one or more of (w/v): creatine (0.001-30%), inosine (0.001-30%), choline chloride (1-30%), sodium chloride (2-30%), magnesium chloride (1-20%), L-arginine (0.1-25%), and/or theophylline (0.1-20%). In some cases, the cream may also contain L-arginine hydrochloride (0-12.5% w/v) and/or theophylline (0-10% w/v). The percentages of each compound can vary (or the compound may be absent in some cases), for example, 1%, 2%, 3%, 4%, 5%, 6%, 7%, 8%, 9%, 10%, 11%, 12%, 13%, 14%, 15%, 20%, etc. In these examples, choline chloride, sodium chloride and magnesium chloride can provide a high ionic strength environment.

In certain aspects of the invention, multiple treatments of the delivery vehicle may increase the duration of the effects of the beneficial substance, for example two, three, four, five, or more treatments may be applied, depending on the particular application. For example, with repeated administrations, the beneficial effects of each treatment may be extended up to ten or twenty hours after treatment, or more in some cases. Such treatments may be given at any suitable frequency, depending on the particular application, for example, every 4 hours, every 8 hours, every 12 hours, every 18 hours, every 1 day, every 2 days, every 3 days, every week, etc. For instance, the treatment may be provided between about 2 and about 30 times within a time period of about 30 days. In some cases, the first treatment may be given at a higher level or concentration than subsequent treatments.

The following examples are intended to illustrate certain embodiments of the present invention, but do not exemplify the full scope of the invention.

EXAMPLE 1

In this example, a 57 year old woman with severe arthritis in her hands and fingers applied a cream comprising a hostile biophysical environment, along with 10% w/v ibuprofen and 12.5% w/v L-arginine, to her hands. She rubbed the cream into the skin of her hands and fingers until completely absorbed. Within 10 minutes she noticed substantial relief from the pain. Within 30 minutes the pain was completely gone. Pain relief persisted for several hours.

EXAMPLE 2

In this example, a 37 year old man with shoulder pain applied a cream comprising a hostile biophysical environment, along with 10% w/v ibuprofen and 12.5% w/v L-arginine, to the painful shoulder. He rubbed the cream in until it was completely absorbed. Within 30 minutes the pain was completely gone. The pain never returned.

EXAMPLE 3

A 54 year old woman with a severe headache in her right temple applied a cream comprising a hostile biophysical environment, 10% w/v ibuprofen, and 12.5% w/v L-arginine to the painful temple. She rubbed the cream in until completely absorbed. Within 10 minutes substantial relief of the headache was achieved. Within 20 minutes the pain was gone. The pain never returned.

EXAMPLE 4

A 33 year old woman with a history of genital herpes infection was treated with a topical transdermal preparation of acyclovir. Herpes is characterized by outbreaks which start as a red, sometimes itching area and progress to open sores. The acyclovir preparation included a hostile biophysical environment, 2.5% w/v acyclovir, and 12.5% w/v L-Arginine. This preparation was applied as soon as the red and sometimes itching areas appeared. This treatment resulted in regression of the insipient herpes outbreak, returning the area to normal within two days and preventing the open sores from developing.

EXAMPLE 5

A 58 year old man suffering from claudication of the lower leg applied a cream comprising L-arginine hydrochloride (12.5% w/v), choline chloride (10% w/v), magnesium chloride (5% w/v), and sodium chloride (5% w/v) in a penetrating base to his legs nightly. After using it daily for three days, the cramps from claudication never recurred as long as he continued daily use of the cream.

EXAMPLE 6

A 72 year old man with a twelve year history of PAD and claudication severely incapacitating him was treated in this example. He began daily use of a cream containing L-arginine hydrochloride (12.5% w/v), choline chloride (10% w/v), magnesium chloride (5% w/v), and sodium chloride (5% w/v) in a penetrating base to his lower legs. After three days of use the frequency of the attacks were markedly reduced, and after ten days the attacks had ceased. Continued daily use of the cream continued to prevent attacks.

EXAMPLE 7

Circulatory impairment and its sequlae have long been known to be a major complication of diabetes. For instance, it has been shown that, in diabetes, the functionality of the endothelial nitric oxide (NO)/nitric oxide synthase (eNOS) system is impaired. NO is generated in the endothelium through the oxidation of the amino acid, L-arginine by the enzyme eNOS. NO causes vascular smooth muscle to relax resulting in increased blood flow. In addition to being a substrate of eNOS, L-Arginine facilitates the dimerization of two identical subunits of eNOS, forming a homodimer. The enzyme is only active in the dimeric form. Under proper conditions, dimerization occurs rapidly, on a timescale of minutes. Once formed the dimer is generally stable.

Subjects with diabetes may have abnormally low levels of L-Arginine and elevated levels of the eNOS inhibitor, asymmetric dimethylarginine (ADME) in their plasma. Though the value of increasing L-Arginine levels in cases of impaired circulation is now recognized, practical schemes for therapeutic use of L-Arginine have been illusive. In this example, it was determined whether supplying L-Arginine transdermally would improve vascular function of the feet in patients with diabetes, as indicated by flow and temperature.

The example was designed as a double-blind vehicle-controlled two-period crossover protocol, with washout periods of one week. Sixteen subjects were enrolled and thirteen completed the study (age 56+/−8 yr). After analyzing the data it was shown that the effect of L-arginine persisted throughout the washout periods (Tables 1 and 2, AU standing for Arbitrary Units). Because of this, except for the initial exposure of L-arginine on virgin feet, the analysis was altered to determine the effect from cumulative exposure to L-arginine throughout the protocol. Blood flow was measured at the metatarsal and Achilles area using a Doppler flow meter, and temperature was measured at the metatarsal and big toe areas using an infrared thermometer. The active cream was a water-based moisturizing vehicle containing 12.5% L-arginine hydrochloride in a hostile biophysical environment comprising a high concentrations of choline chloride, sodium chloride and magnesium chloride. The control vehicle was identical, except that the L-arginine was omitted.

At the first visit, after baseline measurements were made each subject rubbed active cream (4 mg of L-arginine/cm$^2$) into one foot and vehicle into the other. After thirty minutes measurements were made again. A one week wash out period followed. Patients returned after the wash out period and flow and temperature measurements were made. They were then randomly given either active or placebo cream and told to rub it into their feet in the morning and evening every day for two weeks. At the end of two weeks subjects returned and again measurements were made. A second one week wash out period followed that third visit. At the end of that period subjects returned and measurements were made. They were given the cross over product and told again to rub it into their feet morning and evening for two weeks. The subjects returned for final flow and temperature measurements at the end of that period.

At the first visit flow was increased at the Achilles in the foot with active cream from 8.1+/−3.3 to 11.5+/−5.5 (p=0.05) thirty minutes after application. In the foot that received placebo cream flow failed to increase (8.1+/−1.4 vs. 8.3+/−2.2). Further, at the last visit the temperature at the metatarsal area had risen from the initial value of 82.0+/−2.3 to 86.9+/−2.4 (p<0.0001) and the temperature of the big toe had risen from the initial visit value of 74.4+/−4.2 to 82.4+/−4.8 (p<0.0001). At the last visit the flow at the metatarsal area had risen from 8.7+/−4.3 to 11.6+/−5.5 (p<0.00011) and flow at the Achilles area had risen from 8.4+/−2.5 to 11.4+/−5.5 (p=0.02). While the failure of the L-arginine effect to wash out removed the opportunity for placebo control, the improvement in temperature and flow were substantial and highly statistically significant. Though puzzling, one explanation of the persistence of the L-arginine effect is that the local tissue concentration of L-arginine becomes high enough to cause inactive monomers of eNOS to form active dimers.

Thus, in the patients studied in this example with diabetes, treatment of their feet with a transdermal preparation of L-arginine improved both flow and temperature, and this effect was surprisingly long lasting. Such improvement of compromised local blood flow would be beneficial and could reduce the complications of the disease.

TABLE 1

Effect of Transdermal L-Arginine Cream on Temperature

|  | Metatarsal (° F.) | p vs. Visit 1 | Bis Toe (° F.) | p vs Visit 1 |
| --- | --- | --- | --- | --- |
| Visit 1 | 82.0 +/− 2.3 |  | 74.4 +/− 4.2 |  |
| Visit 2 | 84.1 +/− 3.4 | 0.004 | 77.7 +/− 5.3 | 0.01 |
| Visit 3 | 87.0 +/− 2.4 | <0.0001 | 83.6 +/− 4.9 | <0.0001 |
| Visit 4 | 86.1 +/− 2.4 | <0.0001 | 80.6 +/− 5.4 | <0.0001 |
| Visit 5 | 86.9 +/− 2.4 | <0.0001 | 82.4 +/− 4.8 | <0.0001 |

TABLE 2

Effect of Transdermal L-Arginine Cream on Flow

|  | Metatarsal (AU) | p vs. Visit 1 | Achilles (AU) | p vs. Visit 1 |
| --- | --- | --- | --- | --- |
| Visit 1 | 8.7 +/− 4.3 |  | 8.4 +/− 2.5 |  |
| Visit 2 | 10.8 +/− 5.9 | NS | 8.5 +/− 3.9 | NS |
| Visit 3 | 10.8 +/− 4.8 | 0.05 | 9.2 +/− 3.9 | NS |
| Visit 4 | 11.6 +/− 8.3 | NS | 10.0 +/− 4.2 | 0.06 |
| Visit 5 | 11.6 +/− 5.5 | <0.0001 | 11 |  |

EXAMPLE 8

This example illustrates one method of preparing a transdermal formula of the invention including ibuprofen. The final composition is shown in Table 3. Of course, those of ordinary skill in the art will understand that percentages other than the ones listed below are also possible, according to other embodiments of the invention.

TABLE 3

Example of a Transdermal Preparation

| Water | 49% |
| --- | --- |
| L-Arginine Hydrochloride | 7.5% |
| Ibuprofen (sodium salt) | 7.5% |
| Sodium Chloride | 10% |
| Potassium Chloride | 5% |
| Glyeryl Steareate (SE) | 7% |
| Cetyl Alcohol | 7% |
| Squalene | 2% |
| Isopropyl Mysterate | 1% |
| Oleic Acid | 1% |
| Tween 20 | 2% |
| Butanediol | 1% |

To prepare the formulation in this example, sodium chloride, potassium chloride, L-arginine and ibuprofen were mixed in water, then heated to 74 degrees C. with rapid mixing. In a separate container, the remaining ingredients were mixed together and heated to 74 degrees C. The other ingredients were then added to the water phase at 74 degrees C. with rapid mixing. The mixture was then cooled to room temperature with continued mixing. At this point, an emulsion formed with a relatively thin consistency. The emulsion was then homogenized at high speed at room temperature to thicken the consistency.

According to aspects of the invention described and illustrated herein, beneficial substance(s) (e.g., pharmaceutical agent(s)) may be provided (e.g., in a delivery vehicle) at a concentration of between about 0.1% and about 25% (for example at a concentration of 0.1%, 0.5%, 1%, 2%, 3%, 4%, 5%, 6%, 7%, 8%, 9%, 10%, 11%, 12%, 13%, 14%, 15%, 20%, etc.). However, higher (e.g., above 25%, 30%, 40%, 50% or higher) or lower (e.g., below 0.1%, 0.05% or lower) concentrations of beneficial substance(s) may be used. As used herein (for a beneficial substance or any other compound described herein) a concentration % may be a % by weight, a % by volume, or a % weight by volume. As used herein, a beneficial substance may be, for example, a charged beneficial substance, a non-charged beneficial substance, a beneficial substance that forms hydrogen bonds, a beneficial substance that does not form hydrogen bonds, etc.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A topical delivery vehicle for treating a subject, comprising:
    an oil-based cream comprising a water-containing portion,
        the water-containing portion comprising:

(a) a nitric oxide donor comprising L-arginine and/or L-arginine hydrochloride and/or a derivative of L-arginine, and
(b) ibuprofen, wherein the ibuprofen in the water-containing portion is 7.5% or more by weight,
wherein the water-containing portion has an ionic strength of between about 0.25 M and about 15 M.

2. The delivery vehicle of claim 1, wherein the nitric oxide donor comprises L-arginine.

3. The delivery vehicle of claim 1, wherein the water-containing portion comprises an ionic salt.

4. The delivery vehicle of claim 2, wherein the L-arginine is present at a concentration of at least 0.5% by weight/volume.

5. The delivery vehicle of claim 2, wherein the L-arginine is present at a concentration of between about 0.5% and about 25% by weight/volume.

6. The delivery vehicle of claim 1, wherein the water-containing portion has a pH between about 3 and about 11.

7. The delivery vehicle of claim 3, wherein the ionic salt is present in a concentration of between about 5% and about 50% by weight/volume.

8. The delivery vehicle of claim 3, wherein the ionic salt comprises one or more of sodium chloride, choline chloride, magnesium chloride, calcium chloride.

9. A topical delivery vehicle for treating a subject, comprising:
an oil-based cream comprising a water-containing portion, the water containing portion comprising:
(a) an ionic salt having an ionic strength of between about 0.25 M and about 15 M,
(b) L-arginine and/or L-arginine hydrochloride and/or a derivative of L-arginine, and
(c) ibuprofen at a concentration of 7.5% or more by weight.

10. The delivery vehicle of claim 9, wherein the ionic salt is selected from the group consisting of lithium chloride, sodium chloride, potassium chloride, calcium chloride, magnesium chloride, choline chloride, sodium fluoride and lithium bromide.

11. The delivery vehicle of claim 10, wherein the ionic salt is selected from the group consisting of sodium chloride and potassium chloride.

12. The delivery vehicle of claim 9, wherein the derivative of L-arginine is selected from the group consisting of D,L-arginine, D-arginine, an alkyl ester of L-arginine, an alkyl ester of D-arginine, an L-arginine salt, a D-arginine salt, an alkyl ester salt of L-arginine, an alkyl ester salt of D-arginine, L-arginine glutamate, L-arginine butyrate, L-arginine glycolate, D-arginine hydrochloride, D-arginine glutamate; L-homoarginine, N-hydroxy-L-arginine, nitrosylated L-arginine, nitrosylated L-arginine, nitrosylated N-hydroxy-L-arginine, nitrosylated N-hydroxy-L-arginine, and combinations thereof.

13. The delivery vehicle of claim 9, wherein the L-arginine and/or L-arginine hydrochloride and/or a derivative of L-arginine is present at a concentration of between about 0.5% and about 25% by weight/volume.

14. The delivery vehicle of claim 1, wherein the nitric oxide donor comprises L-arginine hydrochloride.

15. The delivery vehicle of claim 1, wherein the water-containing portion comprising has an ionic strength of between about 1 M and about 15 M.

16. The delivery vehicle of claim 9, wherein the nitric oxide donor comprises L-arginine and/or arginine hydrochloride.

17. The delivery vehicle of claim 9, wherein the water-containing portion comprises an ionic salt at a concentration of between about 5% and about 50% by weight/volume.

18. The delivery vehicle of claim 17, wherein the ionic salt comprises one or more of sodium chloride, choline chloride, magnesium chloride, or calcium chloride.

19. The delivery vehicle of claim 9, wherein the water-containing portion comprising has an ionic strength of between about 1 M and about 15 M.

* * * * *